United States Patent
Kelley

(10) Patent No.: US 9,474,614 B2
(45) Date of Patent: Oct. 25, 2016

(54) ACETABULAR COMPONENTS WITH RADIOLOGICAL MARKERS FOR A HIP REPLACEMENT IMPLANT

(71) Applicant: Scott Kelley, Chapel Hill, NC (US)

(72) Inventor: Scott Kelley, Chapel Hill, NC (US)

(*) Notice: Subject to any disclaimer, the term of this patent is extended or adjusted under 35 U.S.C. 154(b) by 0 days.

(21) Appl. No.: 14/453,383

(22) Filed: Aug. 6, 2014

(65) Prior Publication Data
US 2015/0045905 A1 Feb. 12, 2015

Related U.S. Application Data

(60) Provisional application No. 61/863,644, filed on Aug. 8, 2013.

(51) Int. Cl.
*A61F 2/32* (2006.01)
*A61F 2/34* (2006.01)
*A61F 2/30* (2006.01)

(52) U.S. Cl.
CPC ............ *A61F 2/34* (2013.01); *A61F 2002/302* (2013.01); *A61F 2002/3008* (2013.01)

(58) Field of Classification Search
CPC ................. A61F 2/34; A61F 2002/34; A61F 2002/3008; A61F 2250/0098; A61F 2/32; A61F 2002/3208; A61F 2002/3225; A61F 2002/3233; A61F 2002/3241; A61F 2002/3291; A61F 2002/3403; A61F 2002/30049; A61F 2002/30054; A61F 2002/30056
USPC ........................................... 623/22.15–22.38
See application file for complete search history.

(56) References Cited

U.S. PATENT DOCUMENTS

| | | | | |
|---|---|---|---|---|
| 3,829,904 A | * | 8/1974 | Ling | A61B 17/025 623/22.39 |
| 4,123,806 A | * | 11/1978 | Amstutz | A61F 2/32 623/22.39 |
| 4,224,698 A | * | 9/1980 | Hopson | A61F 2/34 606/91 |
| 4,310,931 A | * | 1/1982 | Muller | A61F 2/36 623/22.4 |
| 5,405,402 A | * | 4/1995 | Dye | A61B 19/54 623/22.38 |
| 5,419,324 A | | 5/1995 | Dillow | |
| 6,454,809 B1 | * | 9/2002 | Tornier | A61F 2/30724 623/22.32 |
| 7,004,972 B2 | | 2/2006 | Yoon | |
| 8,888,861 B2 | * | 11/2014 | Preuss | A61F 2/34 623/22.24 |
| 2004/0236341 A1 | | 11/2004 | Petersen | |

(Continued)

OTHER PUBLICATIONS

Callaghan et al., ed. The Adult Hip. vol. 2, 2nd ed. Chapter 60, pp. 884-910, and Chapter 70, pp. 1025-1035. 2007. Lippincott Williams & Wilkins, Philadephia, PA.

(Continued)

*Primary Examiner* — Alvin Stewart
(74) *Attorney, Agent, or Firm* — Coats & Bennett, P.L.L.C.

(57) ABSTRACT

An acetabular component of a hip replacement implant that is configured to be attached to an acetabulum and to receive a femoral component of the hip replacement implant. The component includes a concave body with a closed end configured to seat against the acetabulum and an open end configured to receive the femoral component. At least one radiological marker is positioned on the body and is visibly distinct from the body on X-ray imaging. The radiological markers may include an elongated shape with a length measured between a first end and a second end. The radiological markers may be shorter than the body such that they do not extend completely around the body and the first and second ends are spaced apart from one another.

19 Claims, 5 Drawing Sheets

(56) References Cited

U.S. PATENT DOCUMENTS

| | | | |
|---|---|---|---|
| 2005/0027192 A1* | 2/2005 | Govari | A61B 5/06 600/424 |
| 2005/0085915 A1* | 4/2005 | Steinberg | A61B 17/1666 623/17.16 |
| 2005/0148843 A1* | 7/2005 | Roose | A61B 17/17 600/407 |
| 2005/0202371 A1* | 9/2005 | McGuire | A61C 8/00 433/201.1 |
| 2005/0261777 A1* | 11/2005 | Jones | A61F 2/30724 623/22.32 |
| 2006/0015186 A1* | 1/2006 | Isaac | A61F 2/34 623/22.38 |
| 2007/0055276 A1 | 3/2007 | Edidin | |
| 2007/0088442 A1* | 4/2007 | Cima | A61B 5/055 623/18.11 |
| 2009/0259311 A1* | 10/2009 | Shterling | A61F 2/30965 623/14.12 |
| 2010/0070046 A1* | 3/2010 | Steinberg | A61B 17/1666 623/22.25 |
| 2011/0046745 A1 | 2/2011 | Daniels et al. | |
| 2011/0112540 A1 | 5/2011 | McLean et al. | |
| 2011/0208318 A1 | 8/2011 | Sudmann | |
| 2012/0157913 A1 | 6/2012 | Aziz et al. | |
| 2012/0184964 A1 | 7/2012 | Hudak, Jr. et al. | |
| 2012/0221115 A1* | 8/2012 | Komistek | A61F 2/32 623/22.15 |
| 2012/0245647 A1 | 9/2012 | Kunz et al. | |
| 2014/0276867 A1* | 9/2014 | Kelley | A61B 17/1746 606/89 |
| 2015/0045905 A1* | 2/2015 | Kelley | A61F 2/34 623/22.24 |

OTHER PUBLICATIONS

Hansen et al. "The Rottinger approach for total hip arthroplasty: technique and review of the literature" Curr Rev. Musculoskelet Med (2011) 4:132-138. Springer, Berlin, Germany.

"Zimmer Natural-Hip™ System Surgical Technique" Informational Booklet. 25 pages. 2005. Zimmer, Inc. Warsaw, IN.

"CPT® 12/14 Hip System. Surgical Technique for Primary Hip Arthroplasty" Informational Booklet. 27 pages. 2002. Zimmer, Inc. Warsaw, IN.

"Alloclassic® Hip System Surgical Technique" Informational Booklet. 20 pages. 2003. Zimmer, Inc. Warsaw, IN.

"ZMR® Hip System" Informational literature, 20 pages. 2003. Zimmer, Inc. Warsaw, IN.

"Zimmer® M/L Taper Hip Prosthesis. Surgical Technique" Informational Booklet. 16 pages. 2010. Zimmer, Inc. Warsaw, IN.

"Synergy Cemented Stem Surgical Technique" Informational Booklet, 31 pages. 2004. Smith & Nephew, Inc., Memphis, TN.

"Synergy Cementless Stem Surgical Technique" Informational Booklet, 32 pages. 2004. Smith & Nephew, Inc., Memphis, TN.

"ZMR Revision Taper Hip Prosthesis, Surgical Technique for Revision Hip Arthroplasty" 26 pages. 1999. Zimmer, Inc. Warsaw, IN.

"Summit® titanium tapered stem." Product description and illustration,1 page. 2001. DePuy Orthopaedics, Inc., Warsaw, IN.

Morrey, Bernard, ed. Joint Replacement Arthroplasty. Chapter 44, pp. 619-638. 1991. Churchill Livingstone, Inc., New York, NY.

"DePuy Revision Solutions. Hip Extraction Instrumentation Product Overview." 16 pages. 2009. DePuy Orthopaedics, Inc. Warsaw, IN.

"Moreland Cementless Hip Revision Instrumentation." Product Overview. 12 pages. 1998. DePuy Orthopaedics, Inc. Warsaw, IN.

* cited by examiner

ACETABULAR COMPONENTS WITH RADIOLOGICAL MARKERS FOR A HIP REPLACEMENT IMPLANT

CROSS-REFERENCE TO RELATED APPLICATION

The present application claims the benefit of U.S. Application No. 61/863,644 filed on Aug. 8, 2013, and entitled Acetabular Components with Radiological Markers for a Hip Replacement Implant. This application is hereby incorporated by reference in its entirety.

BACKGROUND

The present application is directed to radiological markers for identifying the position of an implant and, more particularly, to radiological markers on acetabular components of a hip replacement implant.

In existing hip replacement surgical procedures, the surgeon is often provided with a single X-ray view of the one or more acetabular components that have been implanted into a patient. In most instances, this X-ray is an anterior-posterior (AP) view of the pelvis. It is often difficult to determine the three dimensional placement of the one or more components in just two planes that are visible with this view. It is particularly difficult for the surgeon to determine if they are looking at a mirror image or a correct image. Additionally, obtaining an additional view of the acetabular component during a surgical procedure is difficult or impossible. The additional view requires specific positioning of the patient. This positioning may be difficult or not possible with the available equipment in the operating room during the surgical procedure.

SUMMARY

The patent application is directed to an acetabular component with one or more markings that provide for determining an orientation when implanted in a patient. The one or more radiological markers are used in a manner that allows a surgeon to identify a particular section of the rim of the acetabular component on x-ray imaging and thus the orientation of the component. The one or more radiological markings assist in identifying the three-dimensional acetabular component when viewed on a two-dimensional x-ray image.

One embodiment is directed to an acetabular component that includes a concave body with a closed end configured to seat against the acetabulum and an open end configured to receive the femoral component. The body further includes inner and outer sides, and a circular rim that extends around the open end. At least one radiological marker is on the body and is constructed from a material that is visibly distinct from the body on X-ray imaging. Each of the radiological markers includes an elongated shape with a length measured between a first end and a second end. Each of the radiological markers are positioned at the rim of the open end of the body where the length of the radiological markers is less than a circumference of the body with the first and second ends of the radiological marker being spaced apart.

One of the radiological markers may be positioned along the outer side of the body with an entirety of an outer edge of the marker positioned an equal distance away from the open end.

One of the radiological markers may extend along just the rim of the body and is spaced away from the inner and outer sides of the body.

One of the radiological markers may extend around at last one-half of the circumference of the body.

One of the radiological markers may extend around at least a portion of the rim and the outer side of the body and is spaced away from the inner side of the body.

Each of the radiological markers may be spaced away from the rim of the body.

The acetabular component may also include a liner that is positioned along the inner side of the body and may include a concave shape.

The acetabular component may include one of the radiological markers having a first side and a second side with the first side being in closer proximity to the open end with the sides being parallel over a majority of a length of the marker.

First and second radiological markers may be aligned along the same circumferential portion of the body.

Another embodiment is directed to an acetabular component that includes a concave body with a closed end configured to seat against the acetabulum and an open end configured to receive the femoral component. The body also includes a body radius, an inner side, an outer side, and a rim that extends around the open end and includes a circular shape in a plane perpendicular to a central axis of the body. At least one radiological marker is positioned on the body and is constructed from a material that is visibly distinct from the body on X-ray imaging. One of the radiological markers includes a curved shape that corresponds with the body radius such that the radiological marker extends along the body with the body positioned an equal distance away from the open end along a majority of a length of the marker.

One of the radiological markers may not extend completely around a circumference of the body.

One of the radiological markers may include a pair of parallel upper and lower sides.

One of the radiological markers may be positioned along the outer side of the body at the rim.

A second radiological marker may be positioned on the body and may be spaced away from the first one of the radiological markers. The second radiological marker may be positioned on one of the rim and the outer side of the body and the other radiological marker may be positioned on the other of the rim and the outer side of the body.

The body may include a hemispherical shape.

Another embodiment is directed to an acetabular component that includes a concave body with a closed end configured to seat against the acetabulum and an open end configured to receive the femoral component. The body also includes inner and outer sides, and a circular rim that extends around the open end, and a central axis that extends through the closed end and the open end. At least one radiological marker is positioned on the rim and is constructed from a material that is visibly distinct from the body on X-ray imaging. Each of the radiological markers includes an elongated shape with a length measured between a first end and a second end with the first and second ends being spaced apart along the rim.

The rim may be positioned in a second plane that is normal to the axis with the second plane being spaced apart along the central axis.

One of the radiological markers may be positioned along the rim of the body.

One embodiment is directed to an acetabular component that includes a cup-shaped body with a closed end and an open end, with the open end having a circular cross-sectional shape. A radiological marker extends along a limited circumferential length of the body at the open end. The marker has an elongated shape with opposing ends.

The marker may have a curved shape with a constant radius.

The marker may be positioned on a rim at the open end.

The marker may be positioned on an outer side of the body.

The component may also include a second marker at the open end.

The marker may extend around less than ½ of the body.

Another embodiment is directed to an acetabular component that includes a hemi-spherical body with a closed end and an open end. A radiological marker extends around a limited portion of the body at the open end. The marker has an elongated shape with opposing ends that are spaced apart.

The open end may have a circular cross-sectional shape.

Another embodiment is directed to a method of implanting an acetabular component in a patient. The method includes implanting the component into an acetabulum of a patient, visually examining an x-ray image of the implanted component, and determining an orientation of the component within the acetabulum based on an elongated marker that extends around a limited distance of the component.

The method may include visually examining opposing ends of the marker.

The method may include visually examining an orientation of a curvature of the marker.

The various aspects of the various embodiments may be used alone or in any combination, as is desired.

DETAILED DESCRIPTION

The present application is directed to radiological markers on an acetabular component of a hip replacement implant. The markers are configured to be visible on X-ray imaging to facilitate visually determining the orientation and position of the component. The markers include a curved shape and extend along a limited portion of the component.

Figure 1:
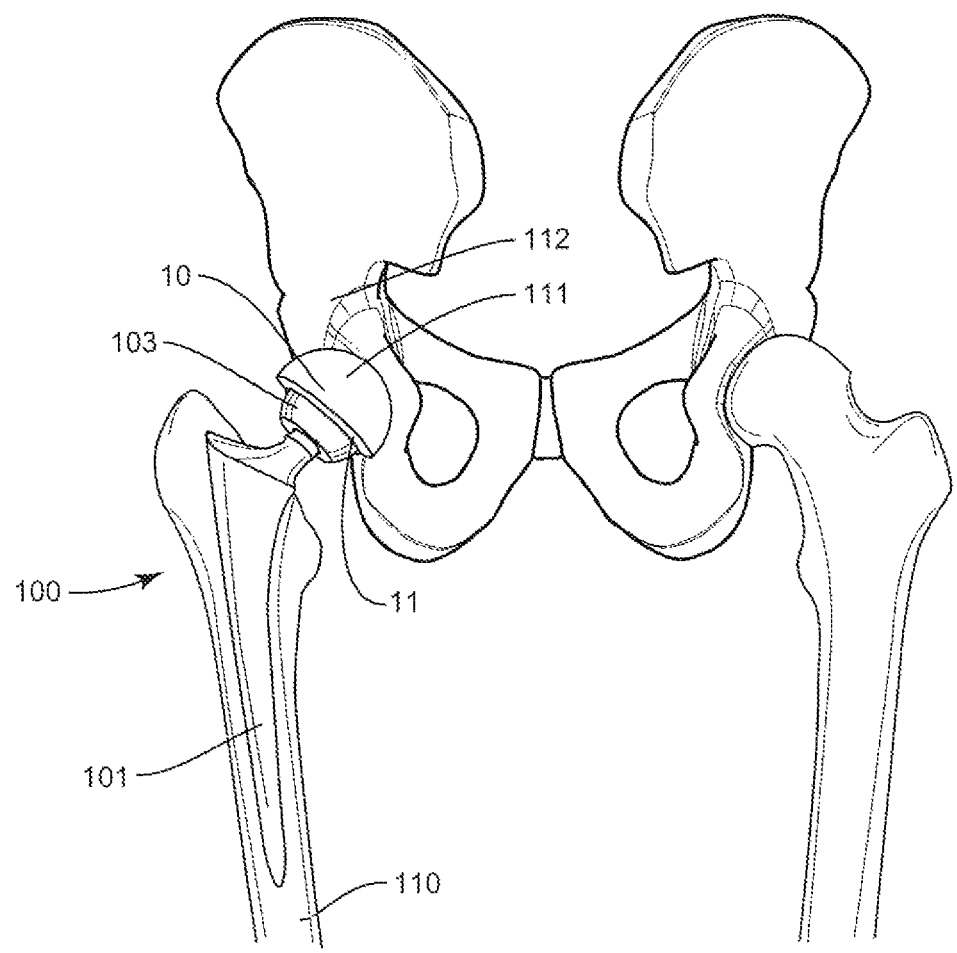
FIG. 1 is a schematic view of a hip replacement implant positioned in a patient.

FIG. 1 illustrates a hip replacement implant 100 positioned within a patient. The implant 100 includes a femoral component 101 that is attached to the femur 110, and an acetabular component 10 that is attached to the acetabulum 111 in the pelvis 112. The femoral component 101 includes a head 103 that seats within a receptacle formed in an open end of the acetabular component 10. This replacement joint replicates the hip joint and provides for pivoting movement of the femur 110 relative to the pelvis 112.

Figure 2:
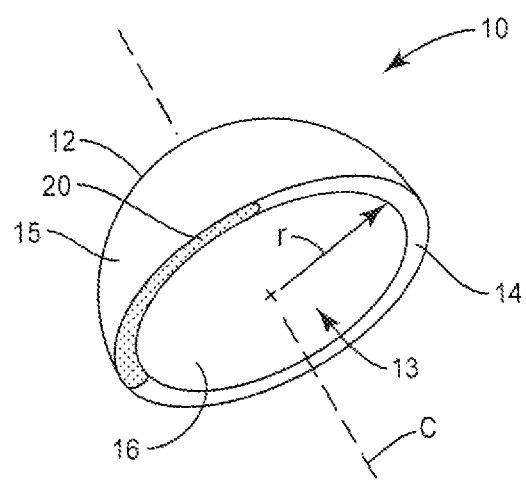
FIG. 2 is a perspective view of a marker positioned on an acetabular component.

The acetabular component 10 includes a semispherical body that is sized to fit within the acetabulum 111. As illustrated in FIG. 2, the component 10 includes an outer side 15 that contacts against the acetabulum 111 and an inner side 16 configured to receive the head 103. The component 10 also includes a closed end 12 that seats against the acetabulum 111, and an open end 13 that forms the receptacle to receive the head 103 of the femoral component 101. A central axis C extends through a center of the component 10 that includes the closed end 12 and the open end 13. The open end 13 further includes a rim 14. The rim 14 extends around the perimeter of the receptacle and may be relatively flat, or may include a rounded shape.

The acetabular component 10 may be constructed as a single unitary piece, or may include multiple pieces. In one embodiment, the acetabular component 10 includes an outer shell and a liner that each includes a concave shape. The shell is configured to be initially attached to the acetabulum 111 with the liner fitting within the shell. The liner includes forms the receptacle sized to engage with the head 103 of the femoral component 101 to form the hip joint.

Examples of hip replacement implants 100 include but are not limited to a Synergy hip system available from Smith & Nephew of Memphis, Tenn., a Summit hip system available from Depuy J&J of Warsaw, Ind., and an Epoc Hip System available from Biomet of Warsaw, Ind.

During the surgical procedure, the acetabular component 10 is positioned in the acetabulum 111. The component 10 should seat properly within the acetabulum 111 to be supported by the pelvis 112, and also to engage with the femoral component 101. During the surgical procedure, X-ray imaging is used to determine the position of the component 10 relative to the pelvis 112. An issue with existing acetabular components is the difficulty in determining their orientation and positioning. This is caused by the circular shape of the open end 12 and the overall hemispherical shape of the component 10. It is particularly difficult to determine the position relative to the coronal and sagittal planes.

It may also be necessary to view an acetabular component 10 at times other than a surgical procedure. This may include a post-operative examination to analyze a recent implant 100, to analyze a damaged implant 100 prior to a revision procedure, and various other occasions.

The present application is directed to an acetabular component 10 that includes one or more radiological markers 20 at the open end 12. This positioning includes the radiological markers 20 located on the rim 14, along the outer side 15 of the body at the rim 14, or a combination of both. The one or more markers 20 allow a surgeon to identify a particular rim section of the acetabular component 10 on x-ray imaging and thus the orientation of the component within the patient. The radiological markers 20 include specific shapes that facilitate the analysis of the orientation of the component 10 when viewed through X-ray imaging. The radiological markers 20 are formed by a material that prevents the penetration of X-rays, such as those used during radiography and fluoroscopy. As such, the markers can be visualized under X-ray imaging. In one embodiment, the markers 20 are opaque on the images thus enhances their visibility. The markers 20 may be constructed from a variety of different materials, including but not limited to platinum, gold, calcium, tantalum, other heavy metals, and combinations thereof.

Figure 2A:
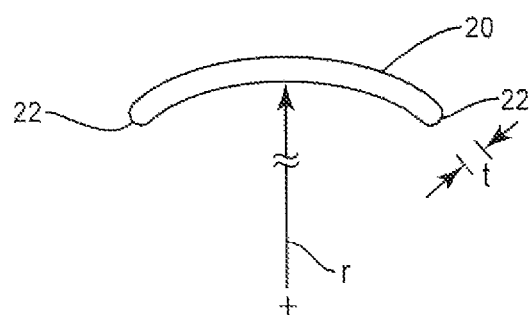
FIG. 2A is a schematic diagram of a marker.

FIG. 2A illustrates a marker 20 that has an elongated shape with opposing ends 22. In this embodiment, the marker 20 includes a constant thickness t along the length. Other embodiments may include a variable thickness along the length. The marker 20 includes a curved shape with a radius r. This radius r may correspond to the radius r of the component 10 (see FIG. 2). The curved shape provides for a viewer to visually determine the orientation of the marker 20 and accompanying component 10. Further, the exposed ends 22 further provide for visually determining the orientation of the marker 20 and component 10. A marker with a circular shape, such as one that extends completely around the component 10 (i.e., 360 degrees), does not provide for visually determining the orientation. This type of marker results in the same visual appearance in multiple different angular orientations within the patient. The elongated, curved shape with defined ends 22 overcomes this problem.

The markers 20 may be positioned at various locations at the open end 12 of the component 10. This may include placement on the rim 14, the outer side 15, the inner side 16, and combinations thereof. Further, a single marker 20 may be positioned on the component 10, or two or more markers 20 may be positioned on the component 10. In embodiments with multiple markers 20, the markers 20 may include configured to provide the same visual appearance on the images, or may be configured to provide different visual appearances. The different visual appearances may be caused by the different markers 20 having different shapes and/or sizes and/or being constructed from different materials.

Figure 3:
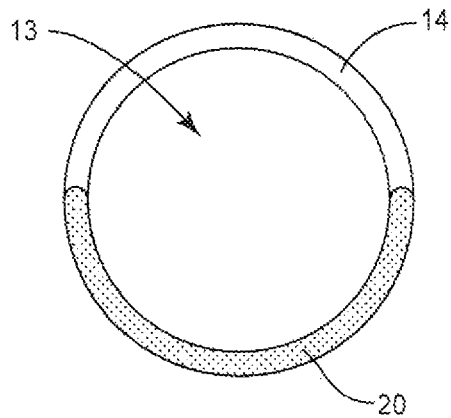
FIG. 3 is an end view of an open end of an acetabular component with a marker.
Figure 4:
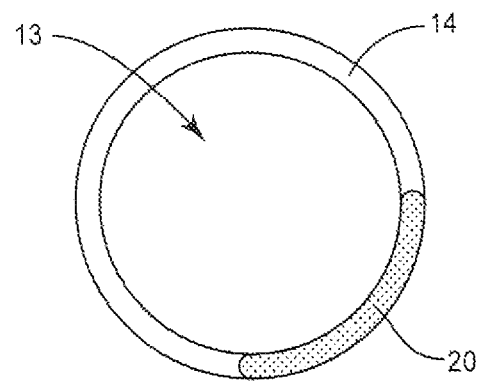
FIG. 4 is an end view of an open end of an acetabular component with a marker.
Figure 5:
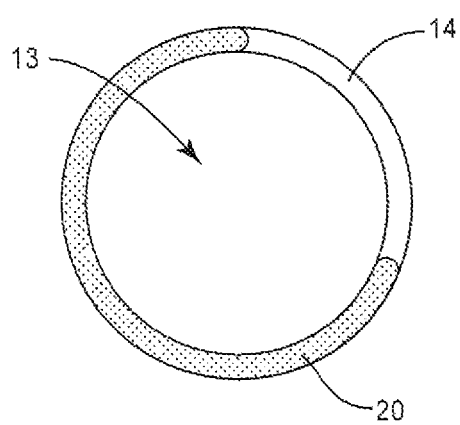
FIG. 5 is an end view of an open end of an acetabular component with a marker.

The markings 20 may span across a variety of distances along the open end 13. In each embodiment, the markings 20 do not extend around an entirety of the open end 13 as this would make it difficult to visually determine the orientation when viewing the component 10 on the images. FIG. 3 includes an embodiment with the marker 20 extending around about one-half of the rim 14. FIG. 4 discloses an embodiment with the marker 20 extending around about one-quarter of the rim 14. FIG. 5 includes an embodiment with the marker 20 extending around about three-quarters of the rim 14.

Figure 6:
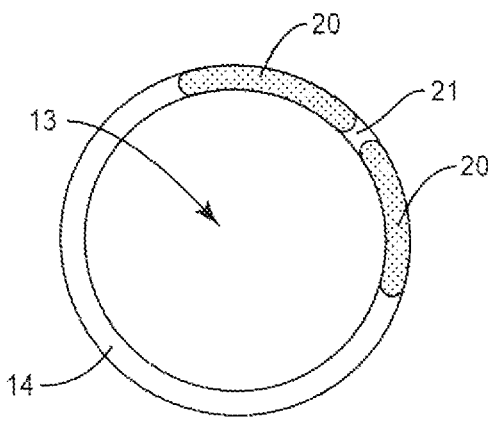
FIG. 6 is an end view of an open end of an acetabular component with a pair of markers.

The markings 20 may be continuous as illustrated in FIGS. 2-5, or may be non-continuous as illustrated in FIG. 6. FIG. 6 includes a pair of markers 20 combined together and extending around about one-third of the rim 14. In embodiments with multiple markers 20, the one or more gaps 21 between the adjacent markers 20 are minimal thus providing for the combination of markers 20 to be differentiated from the non-marked area. This provides for visually distinguishing the marked area of the component 10 to enable a determination of the orientation. In the embodiment of FIG. 6, the gap 21 between the adjacent markers 20 is considerably smaller than the non-marked area.

Figure 7:
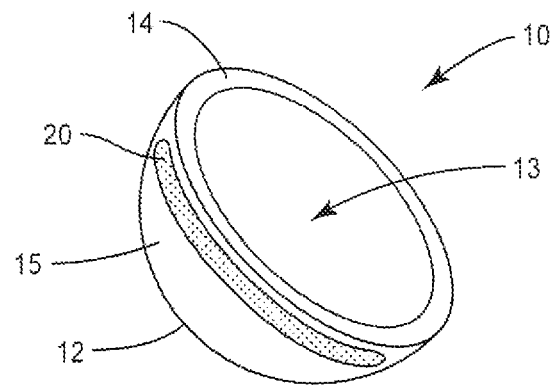
FIG. 7 is a perspective view of a marker positioned on an acetabular component.
Figure 8:
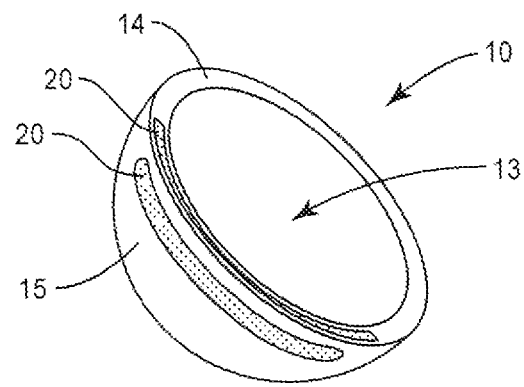
FIG. 8 is a perspective view of a pair of markers positioned on an acetabular component.

FIGS. 7 and 8 include embodiments with markers 20 positioned along the outer side 15 adjacent to the open end 13. The markers 20 are in close proximity to the open end 13. FIG. 8 further includes a second marker 20 on the rim 14. In embodiments with multiple markers, the different markers 20 may each be positioned along the same circumferential portion of the component 10. This leaves the remaining portion of the component 10 unmarked thus allowing for visually differentiating the portions of the component 10 to determine the orientation.

Figure 9:
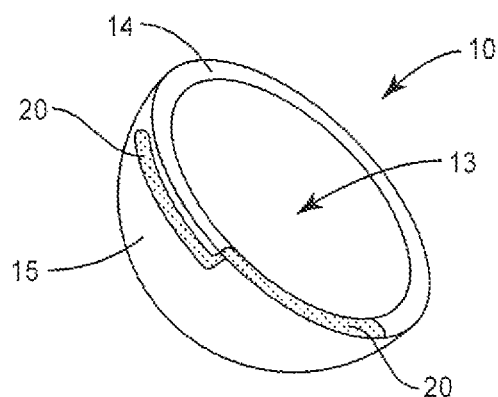
FIG. 9 is a perspective view of a marker positioned on an acetabular component.

FIG. 9 includes an embodiment with a single marker 20 that extends along both the outer side 15 and the rim 14.

Figure 10:
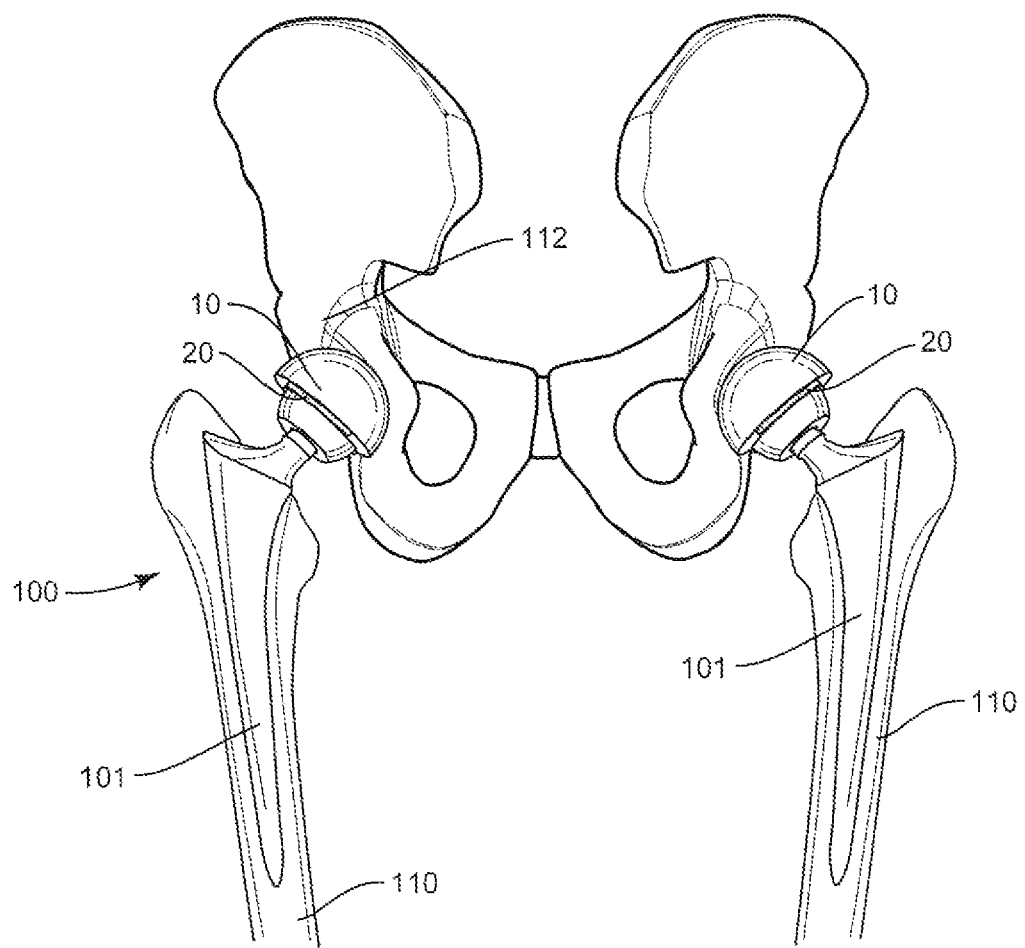
FIG. 10 is an X-ray image of acetabular components each with markers and being positioned in a patient.

FIG. 10 includes an X-ray image of a pair of acetabular components 10 positioned within a patient. The marker 20 on the acetabular component 10 is clearly visible. This allows for an accurate visual determination of the position of the component 10 relative to the pelvis 112. As seen on the left side of the Figure, the marker 20 also provides for visually determining the positioning of the component 10 relative to the femoral component 101.

In one embodiment, the acetabular component 10 includes a shell and an inner liner. Both the shell and liner may include one or more radiological markers 20 or, alternatively just the liner may include the one or more radiological markers 20.

In one embodiment, the positioning of the one or more markers 20 are standardized to identify a particular portion of the component 20 and thus a specific orientation of the acetabular component 10 within the patient. This may include the one or more markers 20 identifying the anterior edge or the posterior edge. In one embodiment in which two acetabular components 10 are implanted, a first component used for the right implant is marked to identify a particular section of the rim (e.g., posterior edge) and a second component that is implanted in the left implant is marked to identify a different particular section of its rim (e.g., anterior edge). In another embodiment, each component is marked and implanted to identify the same particular section (e.g., each of the right and left components are marked to identify the posterior edge). The one or more radiological markers 20 are used in a manner that allows a surgeon to identify a particular rim on x-ray imaging.

The various implants and methods may be used during surgical procedures on living patients. These may also be used in a non-living situation, such as within a cadaver, model, and the like. The non-living situation may be for one or more of testing, training, and demonstration purposes.

Spatially relative terms such as "under", "below", "lower", "over", "upper" and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive.

What is claimed is:

1. An acetabular component of a hip replacement implant configured to be attached to an acetabulum and to receive a femoral component of the hip replacement implant, the acetabular component comprising:
    a concave body with a closed end configured to seat against the acetabulum and an open end configured to receive the femoral component, the body further comprising inner and outer sides, and a circular rim that extends around the open end;

at least one radiological marker on the body and being constructed from a material that is visibly distinct from the body on X-ray imaging, each of the radiological markers comprising an elongated shape with a length measured between a first end and a second end;

each of the radiological markers being positioned at the rim of the open end of the body where the length of the radiological marker is less than a circumference of the body with the first and second ends of the radiological marker being spaced apart.

2. The acetabular component of claim 1, a first one of the radiological markers is positioned along the outer side of the body with an outer edge of the marker positioned an equal distance away from the open end.

3. The acetabular component of claim 1, a first one of the radiological markers extends along just the rim of the body and is spaced away from the inner and outer sides of the body.

4. The acetabular component of claim 1, wherein a first one of the radiological markers extends around at least one-half of the circumference of the body.

5. The acetabular component of claim 1, wherein a first one of the radiological markers extends around at least a portion of the rim and the outer side of the body and is spaced away from the inner side of the body.

6. The acetabular component of claim 1, wherein none of the radiological markers extend on the rim of the body.

7. The acetabular component of claim 1, further comprising a liner that is positioned along the inner side of the body, the liner including a concave shape.

8. The acetabular component of claim 1, a first one of the radiological markers comprises a first side and a second side with the first side being in closer proximity to the open end than the second side, the first and second sides being parallel over a majority of a length of the radiological marker.

9. The acetabular component of claim 1, wherein first and second ones of the radiological markers are aligned along the same circumferential portion of the body.

10. An acetabular component of a hip replacement implant configured to be attached to an acetabulum and to receive a femoral component of the hip replacement implant, the acetabular component comprising:

a concave body with a closed end configured to seat against the acetabulum and an open end configured to receive the femoral component, the body further comprising a body radius, an inner side, an outer side, and a rim that extends around the open end and includes a circular shape in a plane perpendicular to a central axis of the body;

at least one radiological marker positioned at the open end and being constructed from a material that is visibly distinct from the body on X-ray imaging when the acetabular component is viewed with x-ray imaging;

a first one of the radiological markers comprising an elongated curved shape that corresponds with the body radius with opposing first and second parallel sides and opposing first and second ends that are spaced apart.

11. The acetabular component of claim 10, wherein the first one of the radiological markers does not extend completely around a circumference of the body.

12. The acetabular component of claim 10, wherein the first one of the radiological markers is positioned along just the rim of the body and is spaced away from the inner and outer sides.

13. The acetabular component of claim 10, wherein the first one of the radiological markers is positioned along the outer side of the body at the rim.

14. The acetabular component of claim 10, wherein a second one of the radiological markers is positioned on the body and is spaced away from the first one of the radiological markers.

15. The acetabular component of claim 14, wherein the second one of the radiological markers is positioned on one of the rim and the outer side of the body and the first one of the radiological markers is positioned on the other of the rim and the outer side of the body.

16. The acetabular component of claim 10, wherein the body comprises a hemispherical shape.

17. An acetabular component of a hip replacement implant configured to be attached to an acetabulum and to receive a femoral component of the hip replacement implant, the acetabular component comprising:

a concave body with a closed end configured to seat against the acetabulum and an open end configured to receive the femoral component, the body further comprising inner and outer sides, and a circular rim that extends around the open end, the body including a central axis that extends through the closed end and the open end;

at least one radiological marker on the rim and being constructed from a material that is visibly distinct from the body on X-ray imaging when the acetabular component is viewed with x-ray imaging, each of the radiological markers comprising an elongated shape with a length measured between a first end and a second end with the first and second ends being spaced apart along the rim.

18. The acetabular component of claim 17, wherein a second one of the radiological markers is positioned along the body away from the rim with the length being smaller than the body with the first and second ends being spaced apart on the body in a first plane that is normal to the central axis.

19. The acetabular component of claim 18, wherein the rim is positioned in a second plane that is normal to the axis, the second plane being spaced apart along the central axis from the first plane.

\* \* \* \* \*